(12) United States Patent
Burbank et al.

(10) Patent No.: US 7,479,145 B2
(45) Date of Patent: Jan. 20, 2009

(54) TENACULUM-LIKE DEVICE FOR INTRAVAGINAL INSTRUMENT DELIVERY

(75) Inventors: Fred H. Burbank, Laguna Niguel, CA (US); Michael L. Jones, San Clemente, CA (US); Greig E. Altieri, Laguna Beach, CA (US); R. J. Serra, Irvine, CA (US); Ed Olson, Lake Forest, CA (US); Yu-Tung Wong, Irvine, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 595 days.

(21) Appl. No.: 10/716,329

(22) Filed: Nov. 18, 2003

(65) Prior Publication Data

US 2004/0158262 A1 Aug. 12, 2004

Related U.S. Application Data

(63) Continuation-in-part of application No. 10/300,420, filed on Nov. 19, 2002, now abandoned.

(51) Int. Cl.
*A61B 17/42* (2006.01)
*A61B 17/46* (2006.01)
*A61D 1/10* (2006.01)

(52) U.S. Cl. ..................................... 606/119

(58) Field of Classification Search ................ 606/119, 606/205, 208, 210, 211; 600/220, 221, 225–228, 600/29, 135, 184, 196, 197
See application file for complete search history.

(56) References Cited

U.S. PATENT DOCUMENTS

| | | | |
|---|---|---|---|
| 1,571,956 A | * | 2/1926 | Molinelli ..................... 606/119 |
| 2,400,251 A | | 5/1946 | Nagel |
| 3,209,753 A | | 10/1965 | Hawkins et al. |
| 3,320,948 A | * | 5/1967 | Martin ........................ 600/221 |

(Continued)

FOREIGN PATENT DOCUMENTS

DE 195 28 440 A 2/1997

(Continued)

OTHER PUBLICATIONS

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

(Continued)

*Primary Examiner*—(Jackie) Tan-Uyen T. Ho
*Assistant Examiner*—Melanie Tyson

(57) ABSTRACT

The invention is directed to tenaculum-like devices and systems for the intravaginal delivery of therapeutic or diagnostic devices and particularly for occluding a female patient's uterine arteries in order to treat uterine disorders. Included are methods for grasping, manipulating and retaining tissue. The tenaculum-type device has a distal portion with a sound configured to enter a cervical os without causing undue trauma or discomfort to the patient, and a retention or tissue grasping mechanism with a grasping element such as a spike configured to engage and retain a patient's cervix. The tenaculum-type devices embodying features of the invention may have an expandable distal tip to more securely be engaged within the patient's uterine cervical canal.

20 Claims, 9 Drawing Sheets

U.S. PATENT DOCUMENTS

| | | | |
|---|---|---|---|
| 3,411,505 A | 11/1968 | Nobis | |
| 3,777,740 A | 12/1973 | Hokanson | |
| 4,292,960 A | 10/1981 | Paglione | |
| 4,428,374 A | 1/1984 | Auburn | |
| 4,428,379 A | 1/1984 | Robbins et al. | |
| 4,509,528 A | 4/1985 | Sahota | |
| 4,650,466 A | 3/1987 | Luther | |
| 4,757,823 A | 7/1988 | Hofmeister et al. | |
| 4,945,896 A | 8/1990 | Gade | |
| 4,991,588 A | 2/1991 | Pflueger et al. | |
| 4,994,069 A | 2/1991 | Ritchart et al. | |
| 4,997,419 A * | 3/1991 | Lakatos et al. | 604/523 |
| 5,037,430 A * | 8/1991 | Hasson | 606/119 |
| 5,037,433 A | 8/1991 | Wilk et al. | |
| 5,081,997 A | 1/1992 | Bosley, Jr. et al. | |
| 5,108,408 A | 4/1992 | Lally | |
| 5,201,314 A | 4/1993 | Bosley et al. | |
| 5,226,911 A | 7/1993 | Chee et al. | |
| 5,261,409 A | 11/1993 | Dardel | |
| 5,275,166 A | 1/1994 | Vaitenkunas et al. | |
| 5,289,831 A | 3/1994 | Bosley | |
| 5,336,229 A | 8/1994 | Noda | |
| 5,336,231 A | 8/1994 | Adair | |
| 5,368,598 A * | 11/1994 | Hasson | 606/119 |
| 5,383,922 A | 1/1995 | Zipes et al. | |
| 5,456,693 A | 10/1995 | Conston et al. | |
| 5,458,596 A | 10/1995 | Lax et al. | |
| 5,464,409 A * | 11/1995 | Mohajer | 606/119 |
| 5,488,958 A * | 2/1996 | Topel et al. | 600/567 |
| 5,496,331 A | 3/1996 | Xu et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,562,680 A * | 10/1996 | Hasson | 606/119 |
| 5,570,692 A | 11/1996 | Morinaga | |
| 5,588,960 A | 12/1996 | Edwards et al. | |
| 5,598,841 A | 2/1997 | Taniji et al. | |
| 5,614,204 A | 3/1997 | Cochrum | |
| 5,658,299 A | 8/1997 | Hart | |
| 5,662,676 A | 9/1997 | Koninckx | |
| 5,662,680 A | 9/1997 | Desai | |
| 5,665,096 A | 9/1997 | Yoon | |
| 5,672,153 A | 9/1997 | Lax et al. | |
| 5,672,172 A | 9/1997 | Zupkas | |
| 5,691,314 A | 11/1997 | Hodgen | |
| 5,697,937 A | 12/1997 | Toma | |
| 5,697,942 A | 12/1997 | Palti | |
| 5,702,407 A | 12/1997 | Kaji | |
| 5,713,371 A | 2/1998 | Sherman et al. | |
| 5,713,896 A | 2/1998 | Nardella | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,746,750 A | 5/1998 | Prestel et al. | |
| 5,749,879 A | 5/1998 | Middleman et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,895,395 A | 4/1999 | Yeung | |
| 5,899,861 A | 5/1999 | Friemel et al. | |
| 5,904,651 A | 5/1999 | Swanson et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,941,889 A | 8/1999 | Cermak | |
| 5,979,453 A | 11/1999 | Savage et al. | |
| 5,980,534 A | 11/1999 | Gimpelson | |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,039,693 A | 3/2000 | Seward et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,080,118 A | 6/2000 | Blythe | |
| 6,096,051 A | 8/2000 | Kortenbach et al. | |
| 6,106,473 A | 8/2000 | Violante et al. | |
| 6,169,914 B1 | 1/2001 | Hovland et al. | |
| 6,175,751 B1 | 1/2001 | Maizes | |
| 6,186,947 B1 | 2/2001 | Ouchi | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,368,340 B2 | 4/2002 | Malecki et al. | |
| 6,425,867 B1 | 7/2002 | Vaezy et al. | |
| 6,905,506 B2 | 6/2005 | Burbank et al. | |
| 2002/0165579 A1 | 11/2002 | Burbank et al. | |
| 2002/0183771 A1 | 12/2002 | Burbank et al. | |
| 2003/0120306 A1 | 6/2003 | Burbank et al. | |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 | 1/1997 |
| GB | 2 311 468 A | 1/1997 |
| SU | 1 072 859 A | 2/1984 |
| WO | WO 95/02370 | 1/1995 |
| WO | WO 95/02371 | 1/1995 |
| WO | WO 96/05776 | 2/1996 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 02/39904 A1 | 5/2002 |
| WO | WO 02/078521 | 10/2002 |

OTHER PUBLICATIONS

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50 (7-8):337-339 (1998).

Brohim, Robert M. et al., "Development of Independent Vessel Security After Ligation With Absorbable Sutures or Clips", *The American Journal of Surgery,* Mar. 1993, vol. 165, pp. 345-348.

Burbank, Fred at al., "Uterine Artery Occlusion by Embolization or Surgery for the Treatment of Fribroids: A Unifying Hypothesis- Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostate Gland", Bruel & Kjaer Medical Systems, Inc., advertisement.

International Search Report for PCT/US03/35815 mailed Jun. 30, 2004.

International Search Report for PCT/US2004/038111, mailed May 3, 2005.

Written Opinion for PCT/US2004/038111, mailed May 3, 2005.

Translation of FR 1 220 773.

* cited by examiner

TENACULUM-LIKE DEVICE FOR INTRAVAGINAL INSTRUMENT DELIVERY

RELATED APPLICATIONS

This application is a continuation-in-part of application Ser. No. 10/300,420, filed on Nov. 19, 2002 now abandoned, which is relied upon for priority and which is incorporated herein in its entirety.

FIELD OF THE INVENTION

The invention generally relates to the field of holding and manipulating body tissue such as a female patient's uterine cervix in the treatment of various uterine disorders.

BACKGROUND OF THE INVENTION

It is often desirable to hold, maneuver, and retain tissue during medical procedures. Devices for gripping, holding, and manipulating tissue are thus often very useful during medical procedures, particularly ones involving tissues, organs, and structures that are relatively inaccessible or otherwise difficult to reach or to retain.

In many medical procedures, it is useful to locate the cervix and cervical os of a female patient. For example, location of the cervical os and cervix is necessary for proper positioning for the performance of a dilatation and curettage procedure. In order to perform a hysterectomy, particularly with a transvaginal approach, it is often useful to grasp the cervix. This may aid in orienting the uterus, in reducing unwanted motion of the uterus during a procedure, or to manipulate the uterus into a favorable position during treatment. Devices and methods for grasping, retaining and manipulating a uterus may be useful in many other medical procedures as well.

A hysterectomy (surgical removal of the uterus) is performed on approximately 800,000 women annually in the United States and is often the therapeutic choice for the treatment of uterine cancer, adenomyosis, menorrhagia, uterine prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, entailing the removal of the uterus and the resulting loss of reproductive function. Thus, any method which can approximate the therapeutic result of a hysterectomy without removing the uterus would be a significant improvement in this field. Newer treatment methods have been developed for some diseases which may spare these women a hysterectomy.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 344; pp. 671-692, incorporated in its entirety herein). This technique is known as "uterine artery embolization". In this technique, uterine arteries are accessed via a transvascular route from a common femoral artery into the left and right uterine arteries and embolic coils are deposited in the uterine arteries to occlude the arterial passageways The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms. See also Burbank, et al., "Uterine Artery Occlusion by Embolization or Surgery for the Treatment of Fibroids: A Unifying Hypothesis-Transient Uterine Ischemia," The Journal of the American Association of Gynecologic Laparoscopists, November 2000, Vol. 7, No. 4 Supplement, pp. S3-S49. U.S. Pat. No. 6,254,801, to Burbank et al., entitled "Methods for Occlusion of the Uterine Arteries," describes numerous devices and methods useful for occluding a uterine artery by penetrating the tissue of the patient to access the uterine artery, which is incorporated herein in its entirety by reference.

However, catheter-based uterine artery embolization under radiologic direction requires specialized equipment and sophisticated procedures. Accordingly, far fewer uterine artery embolizations than hysterectomies are performed for uterine fibroids which are symptomatic.

What is needed, therefore, are devices and methods to locate, retain and manipulate the cervix, uterus and related tissues and near-by anatomical structures that can be used by physicians in a simple clinical setting or environment to aid in therapeutic procedures.

SUMMARY OF THE INVENTION

The invention is directed to tenaculum-type devices for intravaginally guiding therapeutic or diagnostic instruments to a female patient's uterine cervix and related tissue or nearby anatomical structures of the female patient and the methods of using such devices in the treatment of uterine disorders and other maladies.

Devices embodying features of the invention have an elongated guide rail with a distal guide rail portion configured for non-traumatic entry and advancement through the patient's vaginal canal into the patient's cervical os. In addition to the guide rail, the device has a tissue grasping mechanism secured to a distal portion of the guide rail proximal to the distal tip for gripping the patient's uterine cervix and related tissue or near-by anatomical structures.

The tissue grasping mechanism is secured to the guide rail so as to not interfere with the advancement of a therapeutic or diagnostic instrument over the guide rail to the patient's uterine cervix. The tissue grasping mechanism preferably has a first elongated member or handle with a proximal section configured for manual manipulation outside of the patient and a distal section with a distal end secured to a distal portion of the guide rail proximal to the atraumatic distal tip. The tissue grasping mechanism also has a second elongated member or handle with a proximal section configured for manual manipulation outside the patient in conjunction with the proximal section of the first elongated member and a distal section with a tissue grasping distal end. The second elongated member is pivotally connected to the first elongated member at a pivot point proximally spaced from the distal end of the first elongated member so that the tissue grasping distal end of the second elongated member grasps uterine cervical tissue or related tissue or near-by anatomical structure against the guide rail.

The cervical canal of women who have not given birth is usually sufficiently small that the distal tip of the guide rail fits snugly within the canal. However, with women who have given birth, their cervical canal can be too large to provide a tight fit to the distal end of the guide rail. In those instances, it is recommended that the distal end of the guide rail be configured to expand once inside the patient's cervical canal to provide a better fit within the canal.

A tenaculum-like device having features of the invention may be used to guide, stabilize, anchor, or otherwise control the positional relationship between the patient's uterine cervix and another instrument, such as a uterine artery occlusion device. The tenaculum-like device may be provided with a locking feature, such as conventional ratchet type connectors at the proximal ends of the handles which are effective to maintain the axial position of the guide rail relative to the axis of the cervix while a therapeutic or diagnostic device, such as a uterine artery occlusion device, is mounted on and advanced over the guide rail.

The guide rail on the tenaculum-type device may be provided with an instrument driving mechanism, preferably an instrument driving mechanism which can be operated outside of the patient, when the tenaculum-type device is deployed within the patient's vaginal canal. In one present embodiment, the portion of the guide rail which is proximal to the portion disposed within the patient's cervical canal is at least partially threaded and a driving member with a threaded passageway is mounted on the treaded portion of the guide rail. One or more elongated arms are secured to the threaded driving member and have free ends which extend out of the patient. The physician or other attendant may manipulate the elongated arms to rotate the threaded driving member about the threaded portion of the guide rail. The instrument to perform the procedure is slidably mounted on the guide rail and the threaded drive member on the threaded portion of the guide rail engages the instrument and drives the instrument along the rail to the female patient's uterine cervix, related tissue or near-by anatomical structure.

The one or more handles or proximal extremity of the tenaculum-like device embodying features of the invention may be at least in part detachable so that once an instrument has been put into operative position within the patient's vaginal canal, the one or more handles or proximal portion of the tenaculum-like device which extend out of the patient may be detached from the tenaculum-like device. This allows the distal portion of the tenaculum-like device to be sufficiently contained within the patient's vaginal canal to provide greater mobility and comfort to a patient during treatment.

When using the tenaculum-type device embodying features of the invention, the device is advanced through the patient's vaginal canal, the non-traumatic sound or distal tip of the device is inserted into the patient's cervical os and advanced into the cervical canal. The handles which extend out of the patient are closed together to cause the tissue grasping member on the distal end of one of the handles to grasp the patient's uterine cervix or surrounding anatomical structure to fix the position of the cervix with respect to the guide rail. The medical instrument, such as a uterine artery occlusion clamp or other pressure applying occluding device, is mounted on the guide rail and advanced over the rail until properly positioned adjacent to the patient's vaginal fornix. When the patient's uterine arteries are located (e.g. by Doppler ultrasound blood flow sensors) the pressure applying surfaces of the clamps or other devices are urged against the wall of the patient's vaginal fornix with sufficient pressure to occlude the uterine arteries.

The devices and methods embodying features of the invention thus provide tools and methods to aid in the treatment of uterine diseases and conditions, including uterine fibroids, adenomyosis, dysfunctional uterine bleeding (DUB), post-partum hemorrhage, and other uterine disorders. The devices and methods are simple and easy to use and provide many advantages over other presently available methods and devices for such treatments.

BRIEF DESCRIPTION OF THE DRAWINGS

FIG. 10 illustrates a sound including bifurcated portions that may be used in conjunction with a tenaculum-like device.

DETAILED DESCRIPTION OF EMBODIMENTS OF THE INVENTION

Figures 1, 1A, 1B:
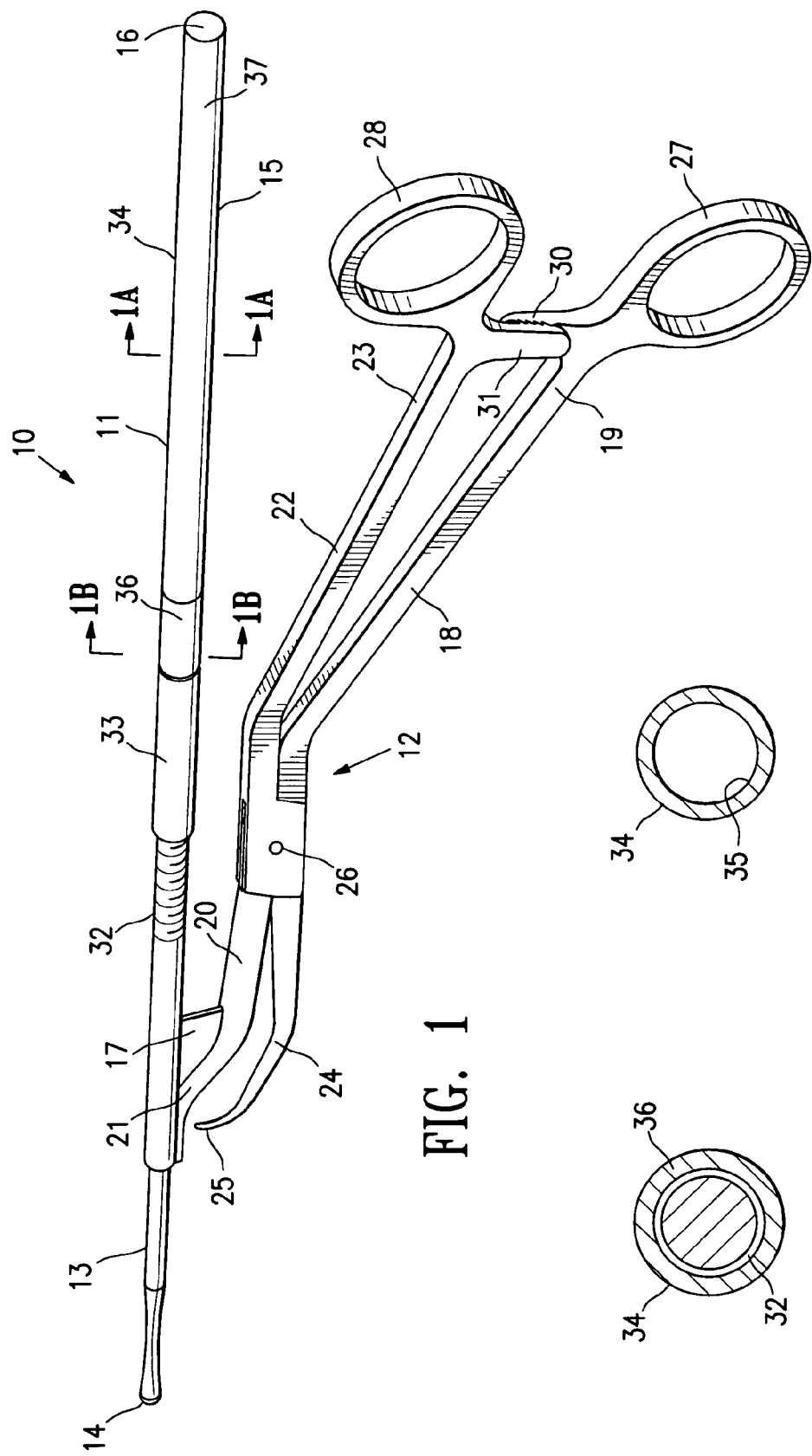
FIG. 1 is a perspective view of a tenaculum-like device embodying features of the invention.
FIG. 1A is a transverse cross-sectional view of the device shown in FIG. 1 taken along the lines 1A-1A.
FIG. 1B is a transverse cross-sectional view of the device shown in FIG. 1 taken along the lines 1B-1B.

FIG. 1 illustrates a tenaculum-type device 10 embodying features of the invention which has an elongated guide rail 11 and an attached tissue grasping mechanism 12. The elongated guide rail 11 has a distal portion 13 with a distal tip or sound 14 and a proximal portion 15 with a free proximal end 16 and is configured to guide a medical instrument (such as an occlusion device shown in FIG. 3) toward the distal portion of the guide rail. The tissue grasping mechanism 12 is secured to the distal portion 13 of the guide rail 11 by connecting plate 17 proximal to the distal tip 14 and is configured to grasp and stabilize the patient's uterine cervix, related tissue or near-by anatomical structure to facilitate delivery of a medical instrument over the guide rail to the patient's uterine cervix.

The tissue grasping mechanism 12 has a first elongated member or handle 18 which has a proximal section 19 configured for manual manipulation and a distal section 20 with a distal end 21 secured to connecting plate 17. The tissue grasping mechanism 12 also has a second elongated member or handle 22 which has a proximal section 23 configured for manual manipulation and a distal section 24 with a tissue grasping distal end or spike 25. The first and second elongated members 18 and 22 are pivotally connected at a pivot 26 proximally spaced from the distal ends of the first and second elongated members 18 and 22. Rotation of the second elongated member 22 about the pivot 26 adjusts the position of the tissue grasping distal end 25 with respect to the guide rail 11 to enable the tissue grasping distal end 25 to grasp uterine cervical tissue against the guide rail 11. In some instances the tissue grasping distal end 25 may penetrate through the cervical wall of the patient. The proximal ends of the first and second elongated members 18 and 22, which are configured to extend out of the patient during the procedure, are provided with finger grips 27 and 28 respectively to facilitate manual manipulation. The proximal ends are also provided with ratcheted locking members 30 and 31 respectively to releasably secure the proximal ends of the elongated members 18 and 22 together.

Figure 2:
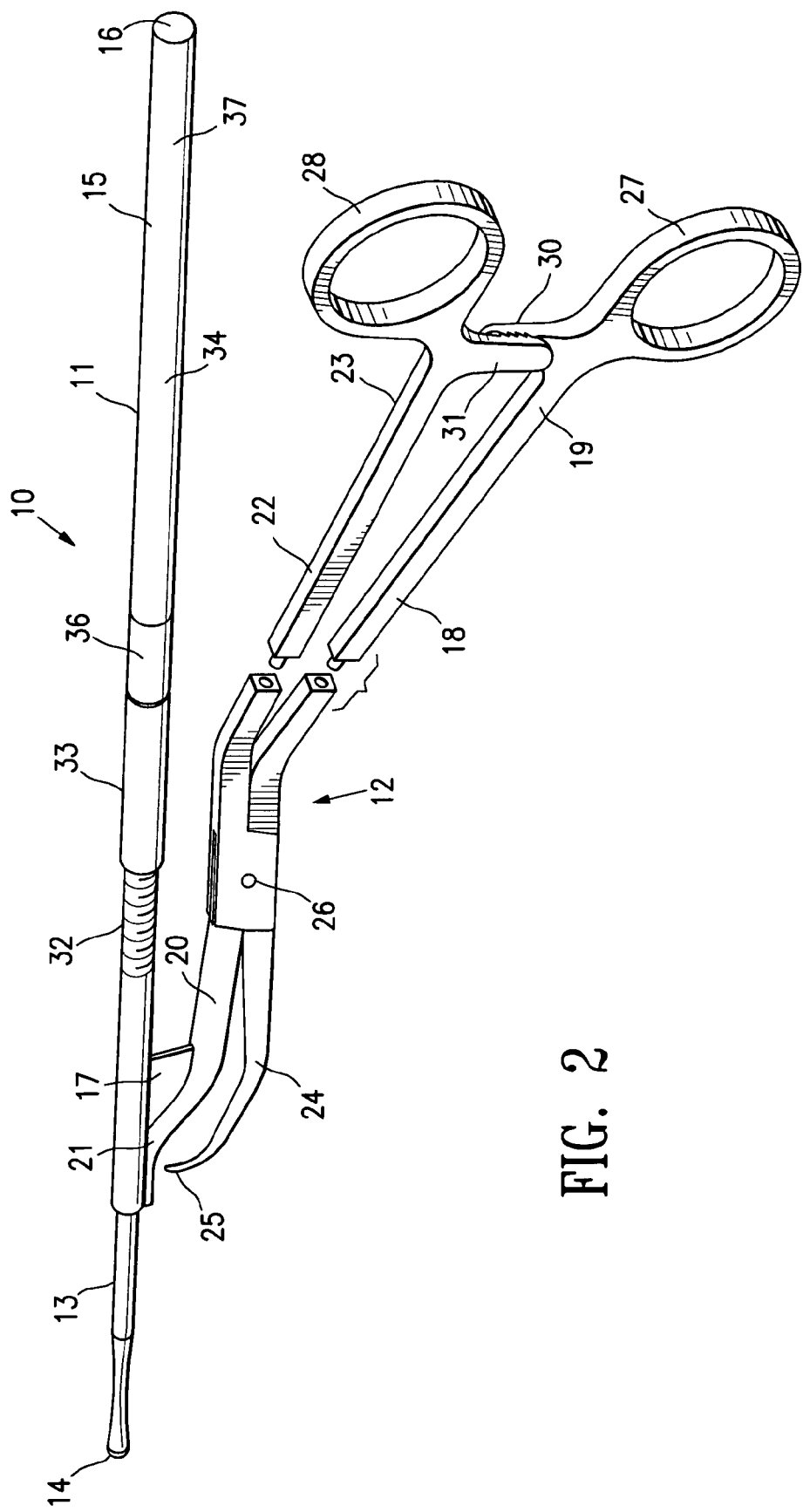
FIG. 2 is a perspective view of a tenaculum-like device similar to that shown in FIG. 1 with removable handles.

The guide rail 11 has a threaded outer portion 32 on at least a portion of its length and a distal collar 33 having internal lumen which allows slidable motion over the threaded outer portion 32 of the guide rail. A driving member 34 forms the proximal portion of the guide rail 11 and has an inner lumen 35 extending therein as shown in FIG. 1A. The connecting member 36 forms the distal end of the driving member 34 and has internal threads which mate with the threads on the threaded outer portion 32 of the guide rail 11. Adjusting knob 37 forms the proximal portion of the driving member 34. Rotation of the knob 37 on the driving member 34 adjusts the position of the distal collar 33 on the threaded outer portion 32 and thereby may drive a treatment or diagnostic device, such as the occlusion device shown in FIG. 2, to the patient's uterine cervix which is slidably mounted on the threaded outer portion 32.

Tenaculum-like devices 10 are configured to engage other therapeutic or diagnostic instruments such as uterine artery occlusion devices which treat uterine disorders by applying pressure to the patient's uterine artery to restrict or terminate blood flow through the artery. One example of such an instrument is uterine artery occlusion device 40 shown in FIG. 3 mounted on tenaculum like device 10. The uterine artery occlusion device 40 has pressure-applying clamping elements 41 and 42 configured to fit on both sides of the patient's uterine cervix and press against the patient's vaginal fornix in order to occlude the patient's uterine arteries. Details of uterine artery occlusion devices with pressure-applying elements are disclosed in co-pending U.S. patent application Ser. No. 10/300,116 filed on Nov. 19, 2002, entitled "Occlusion Device with Deployable Paddles for Detection and Occlusion of Blood Vessels" and application Ser. No. 10/300,495 entitled "Deployable Constrictor for Uterine Artery Occlusion," by Fred H. Burbank et al., assigned to the present assignee Both applications are hereby incorporated by reference in their entirety.

Figure 3:
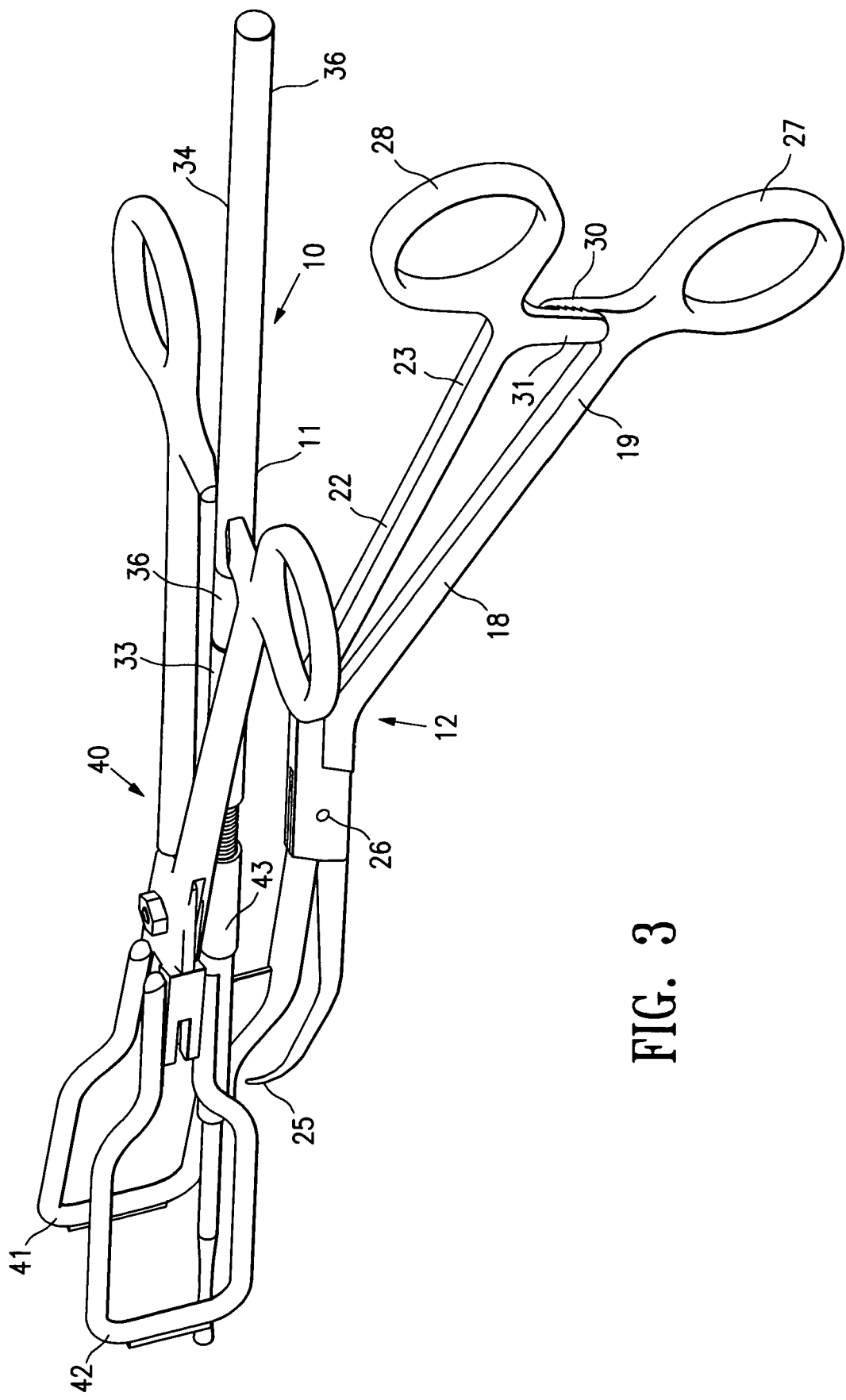
FIG. 3 illustrates a tenaculum-like device as shown in FIG. 1 with a uterine artery occlusion clamp mounted on the guide rail of the tenaculum-like device.

As shown in FIG. 3, uterine artery occlusion device 40 is operatively connected to the guide rail 11 of tenaculum-like device 10 by an attachment sleeve 43, which is configured to at least partially surround or enclose a portion of guide rail 11 so as to be longitudinally movable on the guide rail. Distal sliding movement of attachment sleeve 43 moves uterine artery occlusion device 40 along the path defined by guide rail 11. Movement of the occlusion device 40 along the guide rail 11 may be effected manually, mechanically (such as the drive member 34 by other suitable means. However, as described above, preferably the driving member 34 engages the attachment sleeve 43 (to which the occlusion device 40 is secured) so that rotation of the adjustable knob 36 causes movement of the occlusion device 40 along the guide rail 11.

As shown in FIG. 3, the proximal portions 19 and 23 of the tissue grasping mechanism 12 of the tenaculum-like device 10 may be configured to be removable during use. This allows the distal portion of the tissue grasping mechanism 12 and the guide rail to remain in the patient's vaginal canal during the time period in which the patient's uterine arteries are being occluding by the occluding device 40 mounted on the guide rail 11. Removal of the proximal portions 19 and 23 provides greater comfort and freedom of movement to a patient receiving treatment. The removable proximal portions 19 and 23 may be connected by suitable means such as a threaded connection or with a bayonet-detent connection to the remaining portions of the tissue grasping members.

The tenaculum-like device 10 is inserted into the patient's vaginal canal and advanced therein until the distal tip 14 or sound of the guide rail 11 enters the patient's cervical os. The distal tip 14 of the guide rail 11 is advanced well into the patient's cervical canal for suitable placement that will guide a therapeutic or diagnostic device into a desired location. The tenaculum-like device 10 may be secured in place by pressing the proximal portions 19 and 23 of the first and second elongated members so that the tissue grasping element or spike 25 is pressed into cervical tissue. One or more spikes 25 may be disposed on the distal end of the first elongated member 22 to press into cervical tissue in order to retain the tenaculum-like device 10 in place. It will be understood that other retention elements configured to retain a tenaculum-like device 10 in place within or on a patient's body, such as serrations, grooves, or other elements, may be employed.

Once the tenaculum-like device 10 is secured, an operator may then manipulate the patient's uterine cervix to place the tissue In a desired position or orientation for a subsequent procedure such as uterine artery occlusion. For example, by pulling on the handles 18 and 22 of the tenaculum-like device 10, the tissue next to the cervix, such as the vaginal fornix is stretched, which in turn pulls the uterine arteries towards the vagina so that these arteries are more readily compressed for occlusion. A therapeutic or diagnostic device, such as occlusion device 40, may be attached to the guide rail 11 of tenaculum-like device 10 either before placement of the tenaculum-like device within a patien's vagina or it may be attached at a later time, such as after a tenaculum-like device 10 has been secured to the patient's cervical tissue.

Figure 4:
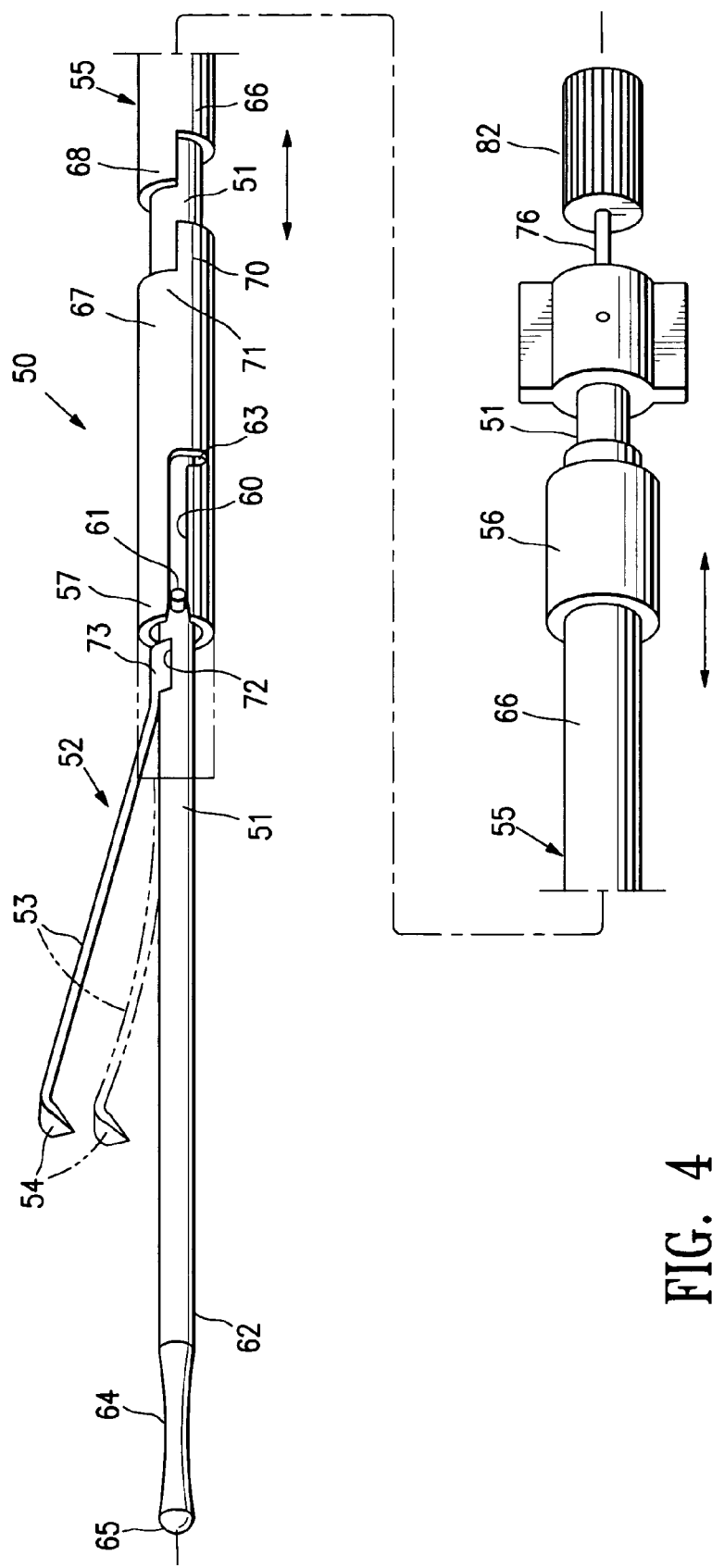
FIG. 4 is a perspective view of another embodiment of a tenaculum like device embodying features of the invention with the tissue grasping element in a disengaged configuration.
Figure 5:
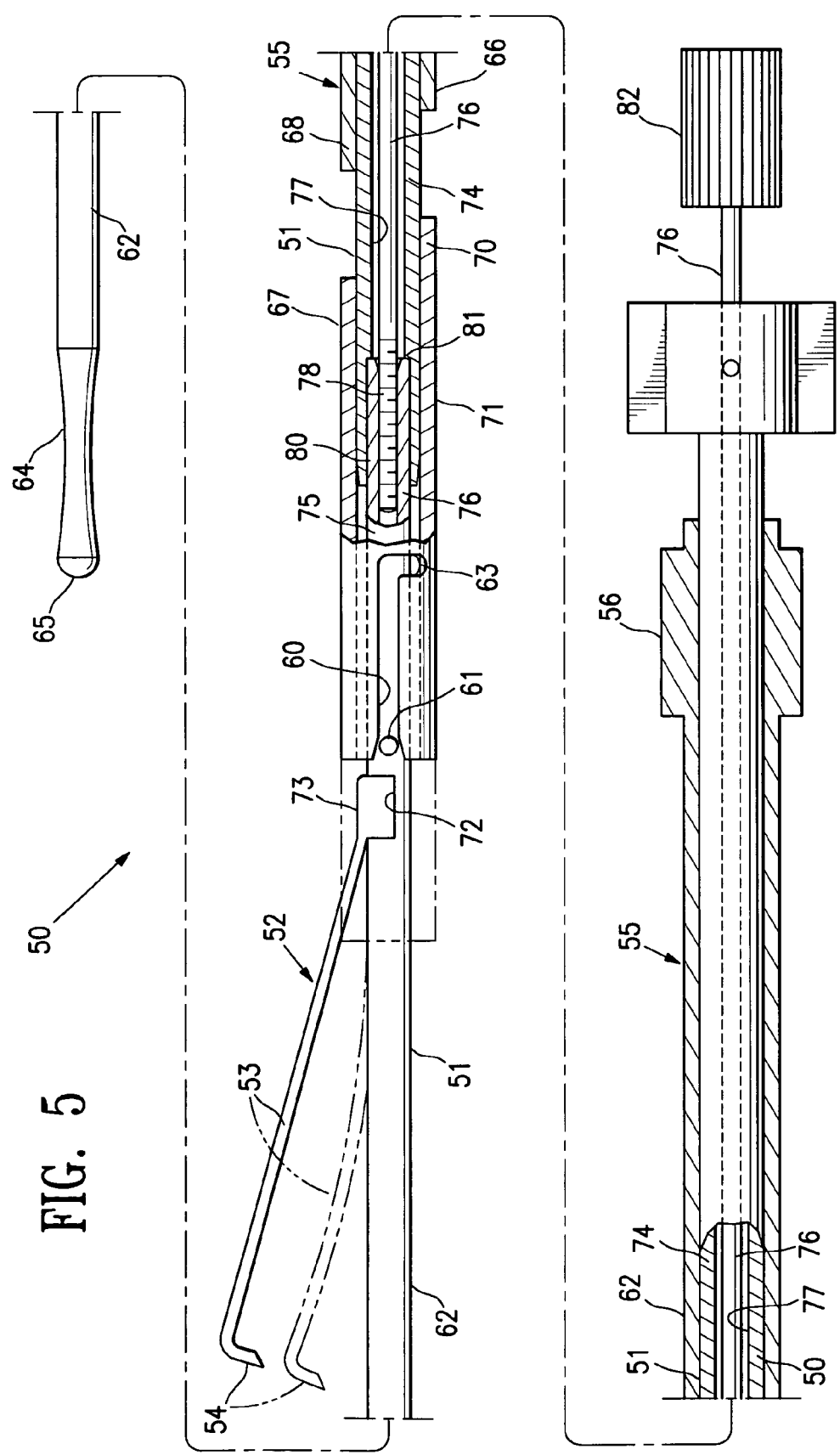
FIG. 5 is a longitudinal cross-sectional view of the tenaculum-like device illustrated in FIG. 4 taken along line 5-5.
Figures 6, 6A:
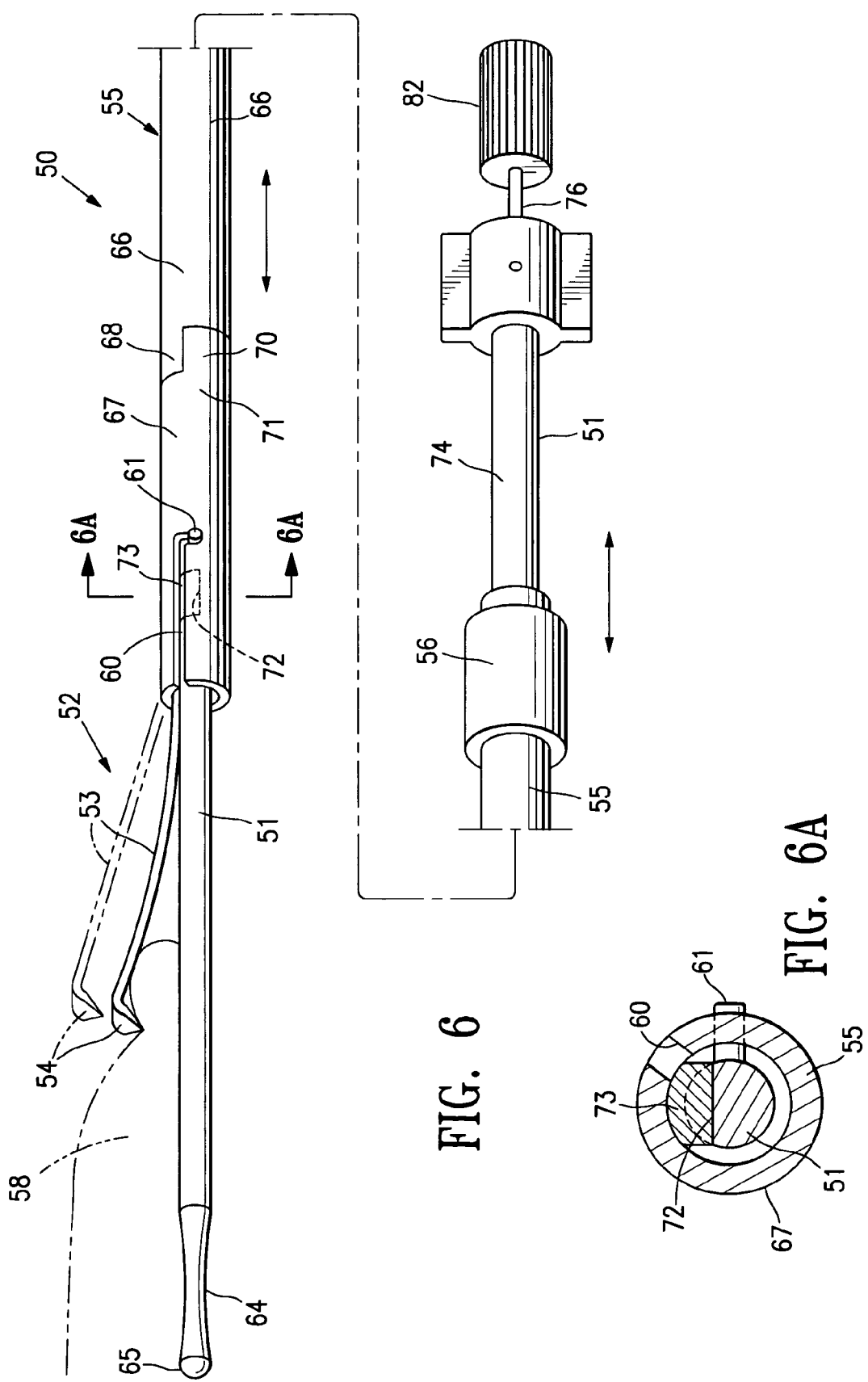
FIG. 6 is a perspective view of the tenaculum-like device shown in FIG. 4 with the tissue grasping element in a tissue engaged configuration.
FIG. 6A is a transverse cross-sectional view of the tenaculum-like device illustrated in FIG. 6 taken along line 6A-6A.

An alternative tenaculum-like device 50 embodying features of the invention is depicted in FIGS. 4-8. The tenaculum-like device 50 has an elongated shaft 51 with a tissue grasping mechanism 52 on the distal portion of the shaft. The tissue gasping mechanism 52 has an elongated arm 53 with a tissue engaging member or spike 54 at the distal end of the arm 53. Outer sheath member 55 is slidably disposed about a portion of the shaft 51 and is provided with handle member 56 for advancing the sheath member over the shaft in order for the distal end 57 of the sheath to slide over the outwardly extending arm 53 to drive the arm toward the shaft 51 and the tissue engaging member or spike 54 into the patient's uterine cervix 58 (which is shown in phantom in FIGS. 6 and 7). The outer sheath 55 has a longitudinally oriented slot 60 which is configured to receive the pin 61 on the distal portion 62 of the shaft 51. The longitudinally oriented slot 60 extends to the circumferentially oriented slot 63 which allows the outer sheath 55 to be locked onto the shaft 51 with the tissue grasping element or spike 54 engaging the patient's uterine cervix 58 as shown in FIG. 6. A wide variety of other locking means may be employed to lock the spike 54 in position. The distal portion 62 of the shaft 51 has a sound 64 with a rounded, non-traumatic distal tip 65.

As shown in FIG. 4-6 the outer sheath 55 is separated into proximal portion 66 and distal portion 67. The distal end of the proximal portion 66 has a semi-circular step 68 which engages the semi-circular step 70 on the proximal end 71 of the distal portion 67 Distal thrusting and rotation of the proximal portion 66 causes the semi-circular steps 68 and 70 to engage, drive and rotate the distal portion 67 so as to place the locating pin 61 on the distal portion of the shaft 51 within the longitudinally oriented slot 60 and ultimately into the locking circumferentially oriented slot 63. As shown more clearly in FIG. 6A, the upper surface of the distal portion 62 of the shaft 51 has a D-shaped recess 72 configured to receive the proximal end 73 of arm 53 to provide a smoother outer surface so that when the distal end 57 of the outer sheath 55 slides distally it slides over the arm so that the spike 54 on the distal end of the arm engages the patient's uterine cervix. The proximal end 73 of arm 53 disposed within the D-shaped recess 72 may be welded, pinned, glued, or otherwise fixedly attached to shaft 14 within the recess. The arm 53 may be made with metal, such as stainless steel, or other durable, flexible material, including polymers. As shown the arm 53 is formed so as to extend radially away from the distal portion 62 of the shaft 51. Alternatively, the joint between the proximal end 73 of arm 53 may include a spring, or a hinged joint, or both so as to bias the distal end of the arm having the tissue grasping element or spike 54 away from the shaft 51 to facilitate receiving the patient's uterine cervix.

Figure 7:
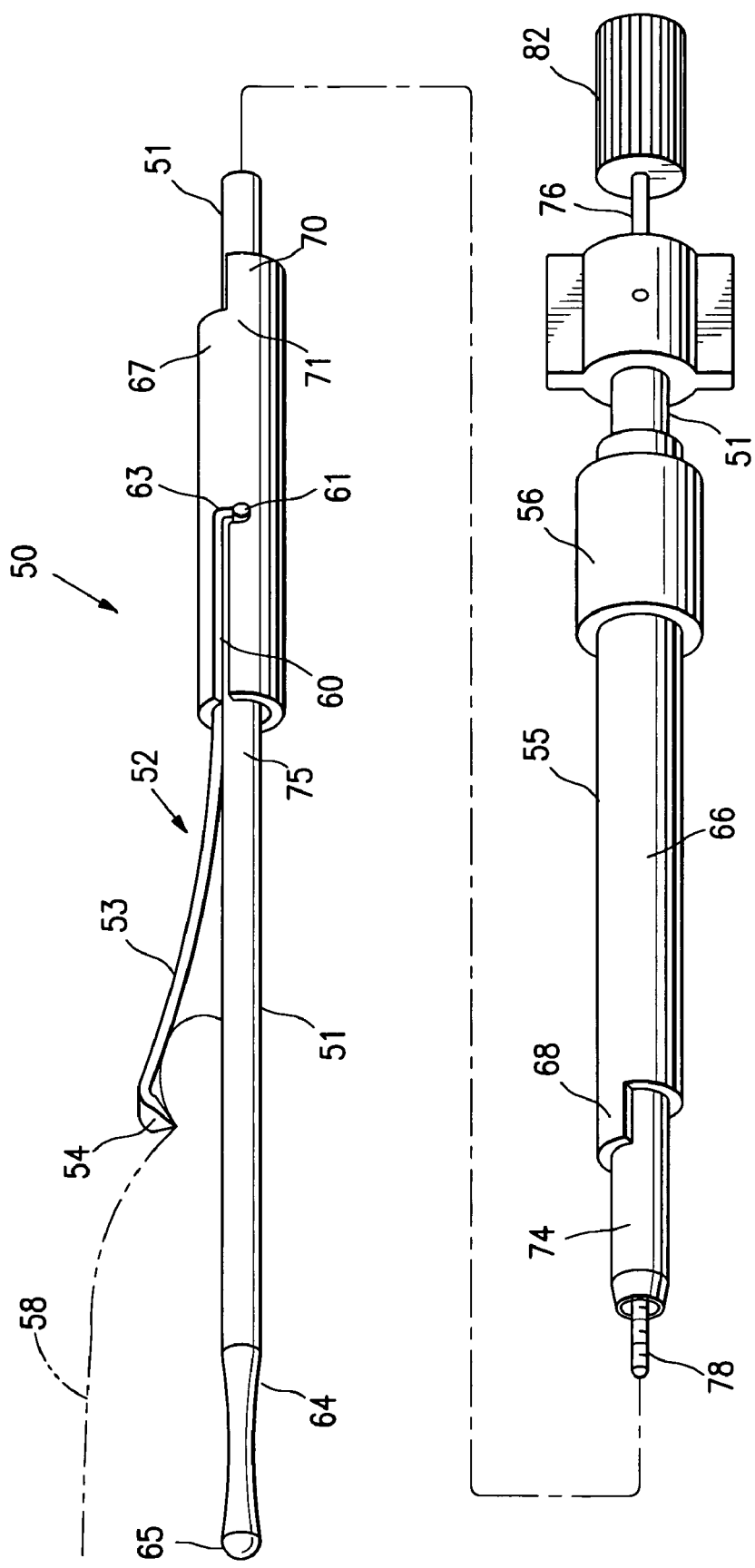
FIG. 7 is a perspective view of a tenaculum-like device as shown in FIG. 4 after separation of a distal portion from a proximal portion.

As best shown in FIGS. 5 and 7, the elongated shaft 51 may be formed of proximal and distal shaft sections 74 and 75 respectively which are held together by elongated threaded member 76 which extends through the inner lumen 77 of proximal shaft section 74 and which has a threaded distal end 78 which is threadably connected to the threaded proximal end 80 of distal shaft section 75. The distal end of the proximal shaft section 74 is provided with an inner shoulder 81 which receives the proximal end 80 of the distal shaft section 75. Clockwise rotation of the enlarged knurled end 82 of the threaded member 76 tightens the connection between the proximal and distal shaft sections 74 and 75.

Once the tenaculum-like device 50 and any device delivered by the tenaculum like device has been intravaginally deployed with the tissue grasping mechanism 52 locked in place, the proximal shaft section 74 and the proximal portion 66 of the of the outer sheath 55 may be detached by rotating the enlarged knurled end 82 in a counter clockwise direction to unscrew the threaded member 76 from the proximal end of the distal shaft section 75, leaving the distal shaft section and the distal portion 67 of the outer sheath 55 so that any device mounted on the tenaculum-like device 10 remains engaged with a cervix 58. This disengagement eliminates the proximal portion of the tenaculum-like device 10 from extending out of a patient's vagina and the accompanying discomfort and inconvenience during a procedure. At the end of the procedure the proximal portion 66 of the outer sheath 55 may be re-engaged with the proximal end of the distal portion 56 of the sheath 55 to unlock the tissue grasping mechanism 12 so that the remainder of the tenaculum-like device 10 and any treatment or diagnostic device still attached to be removed from the patient.

Figure 8:
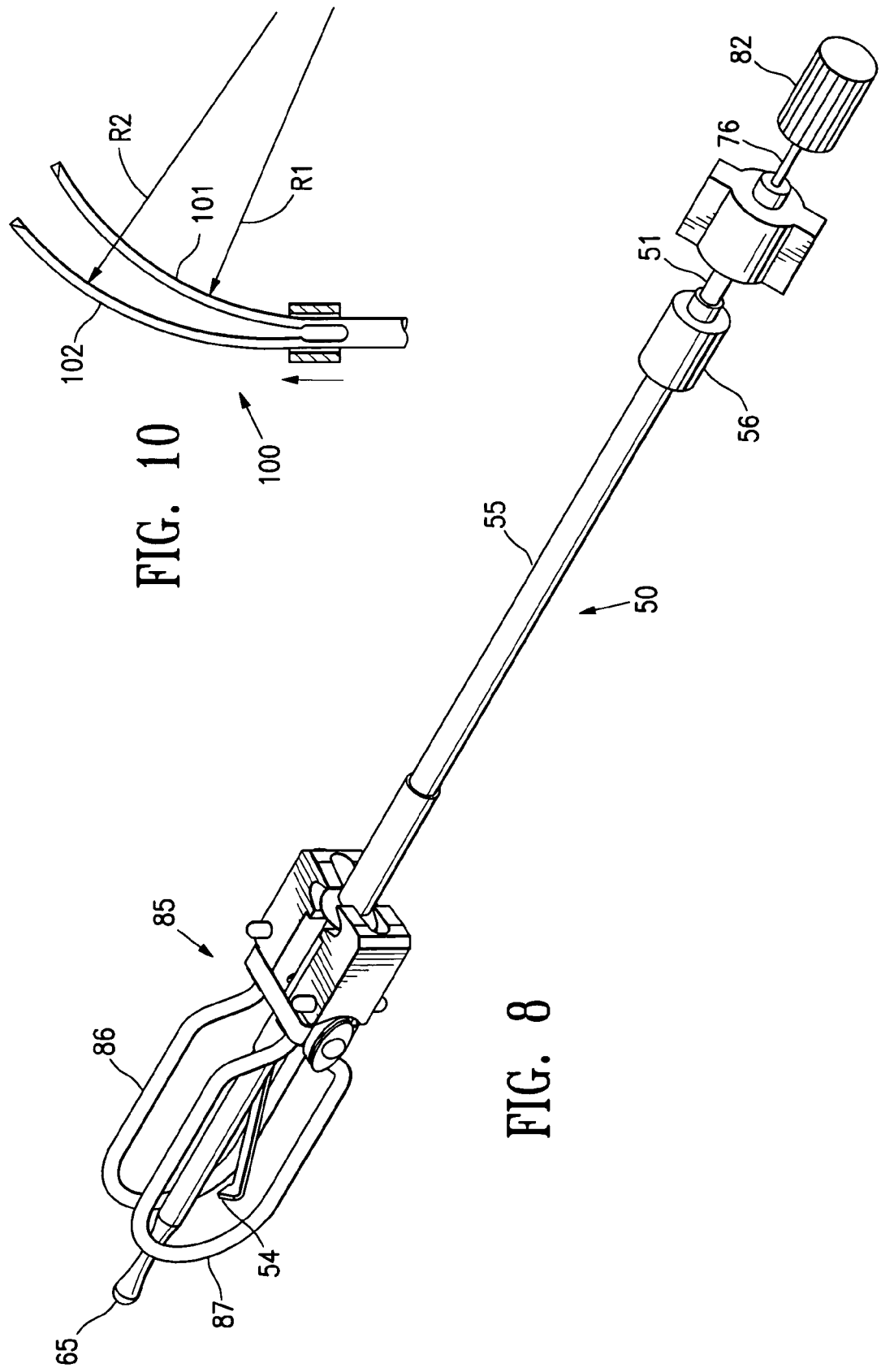
FIG. 8 illustrates a tenaculum-like device as shown in FIG. 4 with a uterine artery occlusion clamp mounted on the guide rail of the tenaculum-like device.

FIG. 8 illustrates a uterine artery occlusion device 85, described in detail in co-pending application Ser. No. 10/300,116, secured to the distal portion of the tenaculum-like device 50. The paddle-like members 86 and 87 are configured to engage both sides of the patient's uterine cervix to occlude both uterine arteries. The occlusion device 85 may be advanced over the tenaculum-like device 50 manually or in a manner similar to that shown in the previously discussed embodiment shown in FIGS. 1-3.

Figure 9:
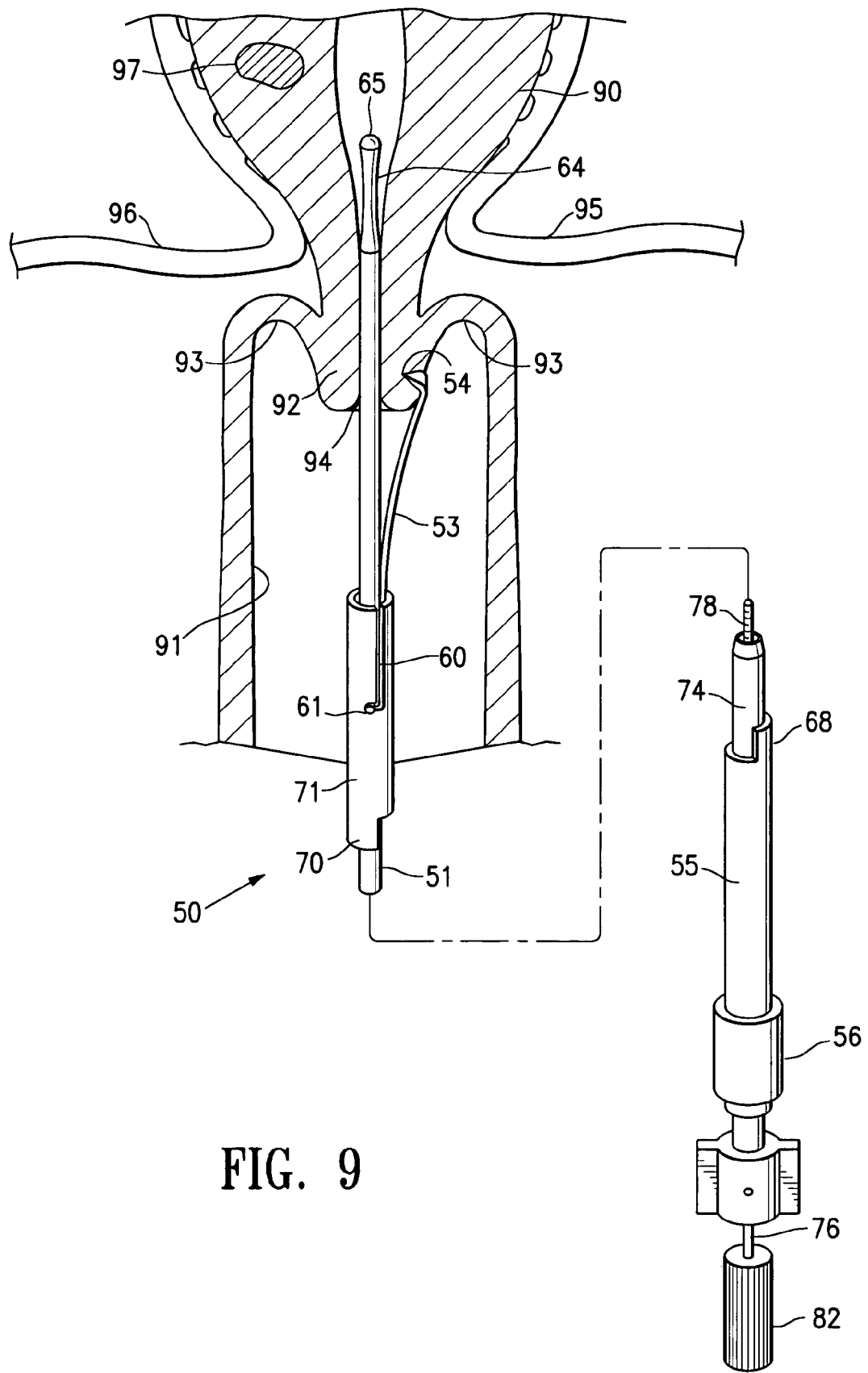
FIG. 9 is a schematic diagram of a reproductive system of a human female illustrating the placement of a tenaculum-like device embodying features of the invention partially disposed within the cervical os of a female human patient.

A schematic diagram of female human reproductive anatomy and related structures is shown in FIG. 9, illustrating the placement and use therein of tenaculum-like device 50 previously described. The anatomical features shown in FIG. 9 include uterus 90, vaginal canal 91, uterine cervix 92, vaginal fornix 93, cervical os 94, and uterine arteries 95 and 96 (which provide a large fraction of the uterine blood supply). A uterine fibroid 97 within the uterine wall is also illustrated. As discussed above, and as disclosed in U.S. application Ser. No. 09/908,815, filed Jul. 20, 2001, to Burbank et al. ("815 application"), co-assigned with the present application, the entire contents of which are incorporated by reference herein, reduction or termination of blood flow in the uterine arteries is effective to treat uterine fibroids and other disorders of a female patient's uterus. The uterus 90 is accessed via vaginal canal 91 and through uterine cervix 92. The vaginal canal 91 has a wall forming the vaginal fornix 93 adjacent uterine cervix 92. The sound 64 extends through the cervical os 94 into the cervical canal 97. Arm 53 is pressed toward the sound 64 so that the spike 54 engages the exterior of uterine cervix 92. With the uterine cervix firmly secured, the tenaculum-type device may be employed to adjust the position of the cervix to facilitate the advancement of medical instruments over the shaft of the tenaculum-like device 50 to the uterus. The uterus 90 is supplied with blood predominantly by the uterine arteries 95 and 96 and with lesser amounts coming from the patient's ovarian arteries. By advancing the uterine artery occlusion device such as that shown in FIG. 8 (or FIG. 3), to press the paddles thereof against the patient's vaginal fornix, the underlying uterine arteries may be occluded when the paddles are close and locked in position.

The uterine cervical canal of a woman who has not given birth is usually tight enough to firmly hold the sound of the tenaculum-type device embodying features of this invention within the canal with the tissue grasping mechanism engaged with the patient's uterine cervix. However, the uterine cervical canal of a woman who has given birth is frequently too dilated to effectively retain the sound within the patient's uterus even with the tissue grasping mechanism engaged with the cervical tissue. For these situations, as shown in FIG. 10, the sound 100 may be expanded to provide a more snug fit within the patient's cervical canal. The curvatures $R_1$ and $R_2$ of the expanded bifurcated portions 101 and 102 of the sound 100 may be varied to provide the desired expansion for effective retention of the sound portions 101 and 102. The bifurcated sound portions 101 and 102 may be held together mechanically or otherwise in an unexpanded condition to facilitate insertion into the patient cervical os. However, once the bifurcated sections 101 and 102 are disposed well within the patient's cervical canal, the restraint used to hold the bifurcated sections together can be removed to allow the expansion of the bifurcated structure. A circular collar 103 may be moved distally along the shaft of the tenaculum type device to close the expanding sound portions 101 and 102. Once the sound 100 is in position within the patient's cervical canal, the restraint collar 103 may be proximally withdrawn from the sound 100 to allow the expansion of the sound portions 101 and 102. The expandable sound 100 may be used in either the embodiment shown in FIGS. 1-3 and the embodiment shown in FIGS. 4-8, previously described.

While particular forms of the invention have been illustrated and described, it will be apparent that various modifications can be made without departing from the spirit and scope of the invention. Accordingly, the invention is not to be limited to the specific embodiments illustrated, but is to be defined by the scope of the appended claims as broadly as the prior art will permit, and in view of the specification if need be. Moreover, those skilled in the art will recognize that features shown in one embodiment may be utilized in other embodiments. Terms such as "element", "member", "device", "section", "portion", "step", "means" and words of similar import when used in the following claims shall not be construed as invoking the provisions of 35 U.S.C. §112(6) unless the claims expressly use the terms "means" or "step" followed by a particular function without setting forth specific structure (in the case of "means") or action (in the case of "step"). All patents and patent applications referred to above are hereby incorporated by reference in their entirety.

What is claimed is:

1. An intravaginal device comprising:
a guide rail having a proximal end, a distal end, and an outer surface extending between the proximal and distal ends thereof, wherein the outer surface of said guide rail includes a threaded section;
a collar mounted on the outer surface of said guide rail and having an internal lumen that allows sliding movement of said collar over the threaded section of said guide rail;
a driving member extending between said collar and the proximal end of said guide rail, said driving member having internal threads for engaging the threaded section of said guide rail;
a tissue grasping assembly including a first elongated element connected with the outer surface of said guide rail, and a second elongated element pivotally connected with said first elongated element and having a tissue grasping element at a distal end thereof; and
a medical instrument slidably mounted on the outer surface of said guide rail between said collar and the connection of said first elongated element with the outer surface of said guide rail, wherein rotation of said driving member in a first direction slides said collar toward the distal end of said guide rail which, in turn, urges said medical instrument toward the distal end of said guide rail.

2. The intravaginal device as claimed in claim 1, wherein said guide rail has a longitudinal axis extending between the proximal and distal ends thereof, and wherein said driving member is rotatable about the longitudinal axis whereby the internal threads of said driving member mate with the threaded section on the outer surface of said guide rail.

3. The intravaginal device as claimed in claim 2, wherein said collar is adapted to slide over the outer surface of said guide rail and along the longitudinal axis of said guide rail.

4. The intravaginal device as claimed in claim 1, wherein said driving member has a proximal end accessible at the proximal end of said guide rail.

5. The intravaginal device as claimed in claim 1, wherein said first elongated element is connected with the outer surface of said guide rail between said collar and the distal end of said guide rail.

6. The intravaginal device as claimed in claim 5, further comprising a connecting plate extending between a distal end of said first elongated member and the outer surface of said guide rail for connecting said first elongated member with the outer surface of said guide rail.

7. The intravaginal device as claimed in claim 6, wherein said medical instrument includes an attachment sleeve for slidably mounting said medical instrument on the outer surface of said guide rail.

8. The intravaginal device as claimed in claim 7, wherein said attachment sleeve at least partially surrounds the outer surface of said guide rail for contacting and sliding over the outer surface of said guide rail.

9. The intravaginal device as claimed in claim 8, wherein a distal end of said collar is adapted to contact said attachment sleeve for urging said attachment sleeve and said medical instrument to slide over the outer surface of said guide rail toward the distal end of said guide rail.

10. The intravaginal device as claimed in claim 9, wherein said connecting plate includes a surface adapted to contact said attachment sleeve for halting sliding movement of said attachment collar toward the distal end of said guide rail.

11. An intravaginal device comprising:
a guide rail having proximal and distal ends, a longitudinal axis extending between the proximal and distal ends, and an outer surface extending between the proximal and distal ends thereof, wherein the outer surface of said guide rail includes a threaded section;
a collar having an internal lumen aligned with the longitudinal axis of said guide rail and being adapted to allow sliding movement of said collar over the threaded section of said guide rail;
a driving member mounted on the outer surface of said guide rail and extending between said collar and the proximal end of said guide rail, said driving member having a distal end with internal threads for engaging the threaded section of said guide rail and a proximal end accessible at the proximal end of said guide rail;
a tissue grasping assembly including a first elongated element having a distal end connected with the outer surface of said guide rail, and a second elongated element pivotally connected with said first elongated element and having a tissue grasping element at a distal end thereof, wherein said driving member is advanceable toward the distal end of said guide rail for urging said collar to slide over the threaded section of said guide rail toward the distal end of said guide rail.

12. The intravaginal device as claimed in claim 11, further comprising a medical instrument adapted to slide over the outer surface of said guide rail.

13. The intravaginal device as claimed in claim 12, wherein said medical instrument includes an attachment sleeve in contact with the outer surface of said guide rail for coupling said medical instrument with said guide rail.

14. The intravaginal device as claimed in claim 13, wherein said attachment sleeve at least partially surrounds the outer surface of said guide rail.

15. The intravaginal device as claimed in claim 14, wherein said attachment sleeve contacts the outer surface of said guide rail during sliding movement of said medical instrument toward the distal end of said guide rail.

16. The intravaginal device as claimed in claim 13, further comprising a connecting plate for interconnecting the distal end of said first elongated element with the outer surface of said guide rail, wherein said connecting plate includes a surface adapted to engage said attachment sleeve for halting distal sliding movement of said attachment sleeve toward the distal end of said guide rail.

17. An intravaginal device comprising:
a guide rail having a proximal end, a distal end, and an outer surface extending between the proximal and distal ends thereof, wherein the outer surface of said guide rail includes a threaded section;
a tissue grasping assembly coupled with said guide rail, said tissue grasping assembly including a first elongated element connected with the outer surface of said guide rail, and a second elongated element pivotally connected with said first elongated element and having a tissue grasping element at a distal end thereof;
a collar mounted on the outer surface of said guide rail and having an internal lumen adapted to slide over the threaded section of said guide rail;
a driving member mounted over the outer surface of said guide rail, said driving member having internal threads for engaging the threaded section of said guide rail; and a medical instrument slidably mounted onto the outer surface of said guide rail between said driving member and the distal end of said guide rail, wherein said driving member is rotatable in a first direction for sliding said collar toward the distal end of said guide rail which, in turn, engages and urges said medical instrument to slide over the outer surface of said guide rail and toward the distal end of said guide rail.

18. The intravaginal device as claimed in claim 17, wherein said guide rail has a longitudinal axis extending between the proximal and distal ends thereof, and wherein said medical device includes an attachment sleeve that at least partially surrounds the outer surface of said guide rail.

19. The intravaginal device as claimed in claim 18, wherein said attachment sleeve is advanceable along the longitudinal axis of said guide rail as said driving member urges said collar and said medical instrument toward the distal end of said guide rail.

20. The intravaginal device as claimed in claim 18, wherein said driving member extends over the outer surface of said guide rail and along the longitudinal axis of said guide rail, and wherein said driving member is accessible at the proximal end of said guide rail.

* * * * *